(12) United States Patent
Sinden et al.

(10) Patent No.: US 7,419,827 B2
(45) Date of Patent: Sep. 2, 2008

(54) CELL LINES

(75) Inventors: John Sinden, Surrey (GB); Kenneth Pollock, Surrey (GB); Paul Stroemer, Surrey (GB)

(73) Assignee: Reneuron Limited, Surrey (GB)

( * ) Notice: Subject to any disclaimer, the term of this patent is extended or adjusted under 35 U.S.C. 154(b) by 0 days.

(21) Appl. No.: 11/283,621

(22) Filed: Nov. 21, 2005

(65) Prior Publication Data

US 2006/0104959 A1   May 18, 2006

Related U.S. Application Data

(63) Continuation of application No. 11/238,702, filed on Sep. 29, 2005.

(30) Foreign Application Priority Data

| Sep. 30, 2004 | (GB) | ................... 0421753.5 |
| Nov. 23, 2004 | (GB) | ................... 0425767.1 |
| Dec. 20, 2004 | (GB) | ................... 0427830.5 |

(51) Int. Cl.
  C12N 5/08    (2006.01)
  C12N 5/00    (2006.01)
  C12N 5/10    (2006.01)
  A61K 48/00   (2006.01)
  A01N 63/00   (2006.01)

(52) U.S. Cl. ...................... 435/368; 435/325; 424/93.2; 424/93.7

(58) Field of Classification Search ........................ None
See application file for complete search history.

(56) References Cited

U.S. PATENT DOCUMENTS

| 5,270,191 | A | 12/1993 | McKay et al. |
| 5,580,777 | A | 12/1996 | Bernard et al. |
| 5,690,927 | A | 11/1997 | Major et al. |
| 5,753,491 | A | 5/1998 | Major et al. |
| 5,770,414 | A | 6/1998 | Gage et al. |
| 5,817,773 | A | 10/1998 | Wilson et al. |
| 5,851,832 | A | 12/1998 | Weiss et al. |
| 5,958,767 | A | 9/1999 | Snyder et al. |
| 6,165,715 | A | 12/2000 | Collins et al. |
| 6,197,585 | B1 | 3/2001 | Stringer |
| 6,200,806 | B1 | 3/2001 | Thomson |
| 6,399,384 | B1 | 6/2002 | Jat |
| 6,465,215 | B1 | 10/2002 | Price et al. |
| 6,528,306 | B1 | 3/2003 | Snyder et al. |
| 6,569,421 | B2 | 5/2003 | Hodges |
| 2001/0001662 | A1 | 5/2001 | Sinden et al. |
| 2002/0028510 | A1 | 3/2002 | Sanberg et al. |
| 2002/0064873 | A1* | 5/2002 | Yang et al. ................... 435/325 |
| 2002/0123143 | A1 | 9/2002 | Toma et al. |
| 2002/0146821 | A1 | 10/2002 | Sanchez-Ramos et al. |
| 2003/0108535 | A1 | 6/2003 | Hodges |
| 2003/0143737 | A1 | 7/2003 | Morrison et al. |
| 2003/0147873 | A1 | 8/2003 | Sinden et al. |
| 2003/0203483 | A1 | 10/2003 | Seshi |
| 2004/0185429 | A1* | 9/2004 | Kelleher-Andersson et al. ............................ 435/4 |
| 2005/0032213 | A1 | 2/2005 | Sinden et al. |

FOREIGN PATENT DOCUMENTS

| WO | WO 89/03872 A1 | 5/1989 |
| WO | WO 89/09816 A1 | 10/1989 |
| WO | WO 91/09936 A1 | 7/1991 |
| WO | WO 92/11355 A1 | 7/1992 |
| WO | WO 93/01275 A1 | 1/1993 |
| WO | WO 93/18137 A1 | 9/1993 |
| WO | WO 96/15226 A1 | 5/1996 |
| WO | WO 97/10329 A1 | 3/1997 |
| WO | WO 98/07841 A1 | 2/1998 |
| WO | WO 00/50568 A2 | 8/2000 |
| WO | WO 01/21790 A1 | 3/2001 |
| WO | WO 01/66698 A1 | 9/2001 |
| WO | WO 01/66781 A1 | 9/2001 |
| WO | WO 01/94541 A2 | 12/2001 |
| WO | WO 03/00868 A1 | 1/2003 |
| WO | WO 03/29432 A2 | 10/2003 |

OTHER PUBLICATIONS

Villa A, Navarro B, Martinez-Serrano A. Genetic perpetuation of in vitro expanded human neural stem cells: cellular properties and therapeutic potential. Brain Res Bull. Apr. 2002;57(6):789-94. Review.*

U.S. Appl. No. 11/178,216, filed Jul. 8, 2005, Sinden et al.

U.S. Appl. No. 09/913,443, filed Aug. 14, 2001, Price.

Allay, J.A. et al. "LacZ and interieukin-3 expression in vivo after retroviral transduction of marrow-derived human osteogenic mesenchymal progenitors" *Human Gene Therapy*, 1997, 8:1417-1427.

(Continued)

*Primary Examiner*—Michael Burkhart
(74) *Attorney, Agent, or Firm*—Saliwanchik, Lloyd & Saliwanchik

(57) ABSTRACT

Genomic instability in T-antigen expressing cells can be overcome by modifying the gene expressing T-antigen so that it lacks Bub1 binding. Stable cell lines can be produced by incorporation of the modified T-antigen gene, preferably together with the catalytic sub-unit of the telomerase construct.

1 Claim, 3 Drawing Sheets

OTHER PUBLICATIONS

Anderson, W.F. "Human gene therapy" *Nature*, 1998, 392:25-30.

Cepko, C.L. "Immortalization of neural cells via retrovirus-mediated oncogene transduction" *Ann. Rev. Neurosci.*, 1989, 12:47-65.

Chen, J. et al. "Intravenous Administration of Human Umbilical Cord Blood Reduces Behavioral Deficits After Stroke in Rats" *Stroke*, 2001, 32:2682-2688.

Chopp, M. et al. "Adult bone marrow transplantation for treatment of stroke in adult mice" *Society for Neuroscience*, 1999, 25:1309, abstract No. 528.2 (abstract).

Cogle, C.R. et al. "Bone marrow transdifferentiation in brain after transplantation: a retrospective study" *Lancet*, 2004, 363(9419):1432-1437, abstract.

Coller, H.A. et al. "Expression analysis with oligonucleotide microarrays reveals that MYC regulates genes involved in growth, cell cycle, signalling, and adhesion" *Proc. Natl. Acad. Sci*, 2000, 973260-3265.

Crystal, R.G. "Transfer of genes to humans: early lessons and obstacles to success" *Science*, 1995, 270:404-410.

Daadi, M.M. and S. Weiss "Generation of tyrosine hydroxylase-producing neurons from precursors of the embryonic and adult forebrain" *J. Neuroscience*, 1999, 19(11):4484-4497.

Deonarain, M.P. "Ligand-targeted receptor-mediated vectors for gene delivery" *Exp. Opin. Ther. Patents*, 1998, 8(1):53-69.

Draper, J.S. et al. "Recurrent gain of chromosomes 17q and 12 in cultured human embryonic stem cells" *Nature Biotech.*, 2004, 22(1):53-54.

Eglitis, M. and E. Mezey "Hematopoietic cells differentiate into both microglia and macroglia in the brains of adult mice" *Proc. Natl. Acad. Sci. USA*, 1997, 94:4080-4085.

Flax, J.D. et al. "Engraftable human neural stem cells respond to developmental cues, replace neurons, and express foreign genes" *Nature Biotech.*, 1998, 16(11):1033-1039.

Frederiksen, K. et al. "Immortalization of Precursor Cells from the Mammalian CNS" *Neuron*, 1988, 1:439-448.

Freed, C.R. et al. "Transplantation of embryonic dopamine neurons for severe Parkinson's Disease" *New Engl. J Med.*, 2001, 344(10):710-719.

Goolsby, J. et al. "Hematopoietic progenitors express neural genes" *PNAS*, 2003, 100(25):14926-14931.

Gray, J.A. et al. "Prospects for the clinical application of neural transplantation with the use of conditionally immortalized neuroepithelial stem cells" *Phil. Trans. R. Soc. Lond. B*, 1999, 354:1407-1421.

Hao, H.N. et al. "Fetal human hematopoietic stem cells can differentiate sequentially into neural stem cells and then astrocytes in vitro" *J. Hematother Stem Cell Res.*, 2003, 12(1):23-32.

Hess, D.C. et al. "Bone marrow as a source of endothelial cells and NeuN-expressing cells after stroke" *Stroke*, 2002, 33:1362-1368.

Hodges, H. et al. "Cognitive Deficits Induced by Global Cerebral Ischaemia: Prospects for Transplant Therapy" *Pharm. Biochem. and Behavior*, 1997, 56(4):763-780.

Inzunza, J. et al. "Comparative genomic hybridization and karyotyping of human embryonic stem cells reveals the occurrence of an isodicentric X chromosome after long-term cultivation" *Mol Human Reprod.*, 2004, 10(6):461-466.

Jat, P. and Sharp, P. "Cell lines established by a temperature-sensitive simian virus 40 large-T-antigen gene are growth restricted at the nonpermissive temperature" *Mol. Cell. Biology*, 1989, 9(4):1672-1681.

Jat, P.S. "Direct derivation of conditionally immortal cell lines from an $H$-$2K^b$-tsA58 transgenic mouse" *Proc. Natl. Acad Sci. USA*, 1991, 88:5096-5100.

Kopen, G.C. et al. "Marrow stromal cells migrate throughout forebrain and cerebellum, and they differentiale into astrocytes after injection into neonatal mouse brains" *Proc. Natl. Acad. Sci USA*, Sep. 1999, 96:10711-10716.

Koshizuka, S. et al. "Transplanted hematopoietic stem cells from bone marrow differentiate into neural lineage cells and promote functional recovery after spinal cord injury in mice" *J. Neuropath. Exp. Neurology*, 2004, 63(1):64-72.

Littlewood, T.D. et al. "A modified oestrogen receptor ligand-binding domain as an improved switch for the regulation of heterologous proteins" *Nucl. Acids Res.*, 1995, 23:1686-1690.

Major, E.O. et al. "Establishment of a line of human fetal glial cells that supports JC virus multiplication" *Proc. Natl. Acad. Sci. USA*, 1985, 82:1257-1261.

McKay et al. "Mechanisms Regulating Cell Number and Type in the Mammalian Central Nervous System" cold Spring Harbor Symposia on Quantitative Biology, 1990, 55:291-301.

McKay et al. "Immortalized Stem Cells Form the Central Nervous System" C.R. Acad. Sci. Paris, Sciences De La Vie, 1993, 316:1452-1457.

Mezey, E. and K.J. Chandross "Bone marrow: a possible alternative source of cells in the adult nervous system" *Euro. J. Pharmacology*, 2000, 405:297-302.

Miller, N. and R. Vile "Targeted vectors for gene therapy" *FASEB J.*, 1995, 9:190-199.

Nakatsuji, T. et al. "Establishment of cell lines from the yolk sac blood islands and paraaortic splanchnopleura of transgenic mouse embryos harboring an immortalizing gene" *Cell Structure and Function*, 1996, 21(6):624.

Netto, C.A. et al. "Foetal grafts from hippocampal regio superior alleviate ischaemie-induced behavioral deficits" *Behavioural Brain Res.*, 1993, 58:107-112.

Okabe et al. "Development of Neuronal Precursor Cells and Functional Postmitotic Neurons from Embryonic Stem Cells in Vitro" Mechanisms of Development, 1996, 59:89-102.

Olanow, C.W. e t al. "A double-blind controlled trail of bilateral fetal nigral transplantation in Parkinson's disease" *Ann Neurol*, 2003, 54(3):403-414.

Ourednik, J. et al. "Neural stem cells display an inherent mechanism for rescuing dysfunctional neurons" *Nature Biotech.*, 2002, 20(11):1103-1110.

Palu, G. et al. "In pursuit of new developments for gene therapy of human diseases" *J. Biotechnology*, 1999, 68:1-13.

Priller, J. "Can adult bone marrow stem cells help repair the brain?" *ACNR*, 2004, 3(6):11-13.

Priller, J. et al. "Targeting gene-modified hematopoietic cells to the central nervous system: use of green fluorescent protein uncovers microglial engraftment" *Nature Med.*, 2001, 7(12):1356-1361.

Rashid-Doubell, F. et al. "Effects of Basic Fibroblast Growth FActor and Gamma Interferon on Hippocampal Progenitor Cells DErived from the H-2Kb-tsA58 Transgenic Mouse" *Gene Ther*, 1994;1(Suppl 1):S63.

Renfranz, P.J. et al. "Region-Specific Differentiation of the Hippocampal Stem Cell Line HiB5 upon Implantation into the Developing Mammalian Brain" *Cell*, Aug. 23, 1991, 66:713-729.

Roy, N.S. et al. "Telomerase immortalization of neuronally restricted progenitor cells derived from the human fetal spinal cord" *Nature Biotech.*, 2004, 22(3):297-305.

Sanberg, P.R. and A.E. Willing "Cellular therapeutic approaches for neurodegenerative disorders" Proceedings of the 1998 Miami Biotechnology Symposium, Feb. 1998, vol. 38, pp. 139-142.

Sanchez-Ramos, J.R. et al. "Expression of Neural Markers in Human Umbilical Cord Blood" *Exp. Neurol.*, 2001, 171:109-115.

Scheffler, B. et al. "Marrow-mindedness: a perspective on neuropoiesis" *Trends Neurosci*, 1999, 22:348-357.

Schmidt, M. et al "A model for the detection of clonality in marked hematopoietic stem cells" *Ann NY Acad Sci*, 2001, 938:146-155.

Sinden, J.D. et al. "Recovery of spatial learning by grafts of a conditionally immortalized hippocampal neuroepithelial cell line into the ischaemia-lesioned hippocampus" *Neuroscience*, 1997, 81(3):599-608.

Snyder, E.Y. et al. "Multipotent Neural Cell Lines can Engraft and Participate in Development of Mouse Cerebellum" *Cell*, Jan. 10, 1992, 68:33-51.

Snyder, E.Y. and J.H. Wolfe "Central nervous system cell transplantation: a novel therapy for storage diseases?" *Curr. Opin. Neurol.*, 1996, 9:126-136.

Snyder, E. Y. et al. "Multipotent neural precursors can differentiate toward replacement of neurons undergoing targeted apoptotic degeneration in adult mouse neocortex" *Proc. Natl. Acad. Sci.*, Oct. 14, 1997, 94(21):11663-11668.

"Stem Cell Markers", Appendix Ei and Eii, p. E1-E11, in *Stem Cells: Scientific Progress and Future Research Directions*, Department of Health and Human Services, Jun. 2001.

Stem Cells: Scientific Progress and Future Research Directions, Jun. 2001, Introductor Chapter and Chapters 8 and 11.

Verma, I.M. and N. Somia "Gene therapy—promises, problems and prospects" *Nature*, Sep. 18, 1997, 389:239-242.

Vescovi, A.L. et al. "Isolation and cloning of multipotential stem cells from the embryonic human CNS and establishment of transplantable human neural stem cell lines by epigenetic stimulation" *Exp. Neurology*, 1999, 156(1):71-83.

Villa, A. et al., "Establishment and properties of a growth factor-dependent, perpetual neural stem cell line from the human CNS" 2000, 161:67:84.

Virley, D. et al. "Primary CA1 and conditionally immortal MHP36 cell grafts restore conditional discrimination learning and recall in marmosets after excitotoxic lesions of the hippocampal CA1 field" *Brain*, 1999, 122:2321-2335.

White, L.A. and S.R. Whittemore "Immortalization of Raphe Neurons: an Approach to Neuronal Function in vitro and in vivo" *J. Chem Neuroanatomy*, 1992, 5:327-330.

Whittemore, S.R. et al. "Isolation and characterization of conditionally immortalized astrocyte cell lines derived from adult human spinal cord" *Glia*, Mar. 1994, 10:221-226.

Wyllie, F.S. et al. "A phenotypically and karyotypically stable human thyroid epithelial line conditionally immortalized by SV40 large T antigen" *Cancer Res.*, 1992, 52:2938-2945.

Gray, J.A. et al. "Conditionally immortalized, multipotential and multifunctional neural stem cell lines as an approach to clinical transplantation" *Cell Transplantation*, 2000, 9:153-168.

Karussis, D. and Slavin, S. "Hematopoietic stem cell transplantation in multiple sclerosis: experimental evidence to rethink the procedures" *J. Neurological Sciences*, 2004, 223, 59-64.

Savitz, S. et al. "Cell therapy for stroke" *NeuroRx*, 2004, 1:406-414.

Silani, V. et al. "Stem-cell therapy for amyotrophic lateral sclerosis" *Lancet*, 2004, 364:200-202.

U.S. Appl. No. 10/570,126, filed Feb. 28, 2006, Roberts et al.

* cited by examiner

CELL LINES

CROSS-REFERENCE TO RELATED APPLICATION

The present application is a continuation of U.S. application Ser. No. 11/238,702, filed Sep. 29, 2005, which is hereby incorporated by reference herein in its entirety, including any figures, tables, nucleic acid sequences, amino acid sequences, and drawings.

FIELD OF THE INVENTION

The present invention relates to the production of cell lines useful in therapy, in particular for transplantation for the treatment of neurological disorders, including stroke, Huntington's disease, Alzheimer's disease, Creutzfeld-Jacob disease and traumatic brain injury.

BACKGROUND TO THE INVENTION

Stroke is the name given to sudden neurological deficits most commonly caused by obstruction or haemorrhage of an artery supplying a region of the brain. Any region of the brain can be affected.

There are an estimated twelve million survivors of stroke in the principal European, American and Japanese markets, with the number of new cases in these markets growing at 7 percent per annum. Approximately 30 percent of stroke patients require ongoing nursing care, estimated to cost between $25 billion to $30 billion per annum in the US alone.

The 20 percent of survivors with moderate or severe disability after stroke are potential candidates for neural stem cell transplantation therapy. Existing drug treatments serving these patients are limited and seek to address the effects rather than the cause of the condition.

Huntington's disease is an uncommon, inherited, progressive and fatal neurodegenerative disorder. In the US, approximately 35,000 patients show overt signs of the disease, with a further 75,000 carrying the abnormal gene. There are no existing treatments for the disease.

Dementia is the most devastating and costly age-related disorder. The most frequently encountered type is senile dementia of the Alzheimer's type (AD), although some (but not all) treatments for Alzheimer's may eventually prove applicable to other dementias. Currently, the cost of caring for Alzheimer's patients, who can no longer safely care for themselves, is estimated to approach $100 billion in the US. Age itself is a risk factor for Alzheimer's, the prevalence of Alzheimer's in the population doubles from age 65 to 75, and again from 75 to 85, at which point 35% show signs of AD. With the ageing of the population, over the next two decades the number of Alzheimer's patients in the US alone will increase from 4-5 million to ten million cases. The social and financial burdens will expand proportionally. Dementia is also seen following loss of blood supply to the brain, for example, following cardiac arrest or some forms of cardiac bypass surgery, also following suffocation or following multiple infarcts in the brain.

Creutzfeld-Jacob disease is a rare disorder, one of a number of transmissible spongiform encephalopathies involving progressive inflammatory neurodegeneration occurring due to the buildup of physicochemically abnormal prion protein. A variant form is seen in cases of variant CJD, a rapidly progressing fatal prion disease mirroring the bovine disorder, "mad cow" disease or bovine spongiform encephalopathy (BSE). The theoretical risk of an epidemic of this disorder in the UK and possibly elsewhere remains, due to the widespread consumption of meat products from BSE-infected cattle during the 1980s and early 1990s.

Traumatic Brain Injury significantly affects over 500,000 individuals annually in the United States alone with a variety of affects from mild concussion to coma and death. 80-85,000 patients annually suffer a head injury that leads to very significant neurological deficit or disability. The estimates of total economic cost place the price tag for TBI at almost $50 billion in the US alone.

Stem cell replacement therapy is seen as a viable treatment option for many diseases including, but not limited to, those described above for which significant cell loss and damage is a cause or consequence. Stem cells can be derived from human tissues at any stage of development, from the early embryo to the adult. Early embryonic stem cells are capable of forming cells from any tissues; however, the cells are likely to form tumours when transplanted. As the tissues develop through the fetal and adult stages, the resident stem cell populations reduce their developmental potential and lose their inherent tumourigenic capacity, becoming somatic stem cells, also known as tissue- or lineage-restricted stem cells. Somatic stem cells are multipotent, that is they are capable of becoming any differentiated cell type from their organ of origin.

Embryonic stem cells can be 'differentiated' or selected to form populations of somatic stem cells, which phenotypically resemble somatic stem cells from fetal or adult tissues and therefore lose their tumorigenic potential (for example, WO03-A-000868). Only somatic stem cells (derived from adult or fetal tissues or differentiated from embryonic stem cells) represent, at the current state of knowledge, safe stem cells for cell therapy. The cell lines described in this invention are examples of somatic neural stem cells.

Somatic stem cells from the brain have been proposed as treatments for intractable neurological disorders including Parkinson's diseases, stroke, Huntington's, and and spinal cord injury. Despite early success in anecdotal clinical reports, controlled transplant studies with primary human fetal brain tissue in Parkinson's disease have, however, failed to deliver any consistent benefits [Freed CR, et al., NEW ENGLAND JOURNAL OF MEDICINE 344 (10): 710-719 MAR. 8, 2001; Olanow et al., ANNALS OF NEUROLOGY 54 (3): 403-414 SEPTEMBER 2003] and widespread clinical application of such transplants is in any case constrained by practical and ethical problems.

The heterogeneity of primary human fetal tissues and cells in terms of both cell purity and quality makes the interpretation of such clinical trials difficult. Alternative products can be built on new knowledge of the potential of stem cells as a source of scalable purified cells and tissues for transplantation. For example, following the demonstration that neuroepithelial stem cells and, significantly, clonal cell lines derived from neroepithelial stem cell populations, can restore functional deficits in animal models of neurological diseases [Sinden et al., NEUROSCIENCE 81 (3): 599-608 DECEMBER 1997; WO-A-9710329; Gray et al., PHILOSOPHICAL TRANSACTIONS OF THE ROYAL SOCIETY OF LONDON SERIES B-BIOLOGICAL SCIENCES 354 (1388): 1407-1421 AUG. 29, 1999], many groups have shown that fetal human neural cells can be expanded for several months in defined media with additional growth factors either as genetically immortalized (by means of the transduction of different immortalizing genes) or as expanded stem cells using specialised culture methods (sometimes referred to as 'epigenetic' methods) [Flax et al., NATURE BIOTECHNOLOGY 16 (11): 1033-1039 NOVEMBER 1998; Vescovi et al., EXPERIMENTAL NEUROLOGY 156 (1): 71-83 MARCH 1999]. Neural stem cells, as described in the prior art, have been transplanted into experimental animals and have shown evidence of survival. However, these cells and cell lines are not suitable for use in human patients due to their uncontrolled provenance and manufacture and have not as yet shown evidence of functional efficacy in validated animal models of human neurological disease.

Real clinical and industrial progress in human stem cell transplantation is dependent upon the availability of cell lines with controlled sources and manufacturing that are able to expand quickly and serve as a sustainable resource, available on demand to a broad population of patients. Cell lines could be specific to individual disorders or general across a class of disorders. In order to achieve this goal, cell lines must be generated with appropriate biological characteristics (tissue or cell specific phenotype) and must be sufficiently robust to survive a scaleable manufacturing process to make master and working cell banks of frozen vials of cells from which reproducible, GMP—compliant, clinical lots and commercially viable product batches can be derived. One approach to this problem is to use an immortalizing gene to safeguard the regenerative potential of a cell line and prevent it from entering early senescence. Examples of immortalising genes that have been used to generate neural stem cell lines include: (1) telomerase reverse transcriptase (hTERT) [Telomerase immortalization of neuronally restricted progenitor cells derived from the human fetal spinal cord Roy N S, Nakano T, Keyoung H M, Windrem M, Rashbaum W K, Alonso M L, Kang J, Peng W G, Carpenter M K, Lin J, Nedergaard M, Goldman S A NATURE BIOTECHNOLOGY 22 (3): 297-305 MARCH 2004], (2) SV40 T antigen [Sinden et al., op cit, WO9710329], (3) combinations of SV40 T and hTERT (WO0121790) and myc proteins [U.S. Pat. No. 5,580,777; Flax et al., op cif]. Genetic overexpression of c-myc, a naturally occurring protooncogene that is normally expressed during cell development, is demonstrated in this invention as a means of stably enhancing cell proliferation and preventing changes in cell karyotype, thereby avoiding transformation of the cell phenotype.

Following from considerable experience in developing stem cell lines as therapeutics, we believe the following represent the key features of a human stem cell line for application in the clinic:

Multipotent cells that can develop into specific cells typical of the tissues that are targeted for transplantation.
Cells that are derived from a single founder cell (clonal cells)
Genetically stable cells with normal chromosomes
Cells that have the ability to differentiate into appropriate cell types, in vitro and in vivo.
Cells that can be grown in large numbers and stored
Cells that are safe, particularly not showing tumourigenic potential
Cells whose migration, once implanted, is limited to areas of tissue damage
Cells that are efficacious in recognised animal models
Cells whose provenance is fully documented While expansion of stem cells on surface or suspension culture is possible without genetic immortalisation ('epigentic' culture), expansion of human neural stem cells is slow and the resulting cultures contain a high proportion of differentiated progeny, which will not survive subculture manipulations [WO99-A-11758, Vescovi et al., op cit]. Further, long term culture of 'epigenetic' stem cells may induce chromosomal alterations that may prevent the clinical application of the cell lines. There are no reports of genetic stability of human epigenetic somatic cell lines, although recent reports have indicated chromosomal aberrations in embryonic stem cell lines at greater passage numbers [Draper et al., NATURE BIOTECHNOLOGY 22 (1): 53-54 JANUARY 2004; Inzunza et al., MOLECULAR HUMAN REPRODUCTION 10 (6): 461-466 JUN. 1 2004].

Therefore, the scalability of epigenetically expanded cell lines is limited from an industrial point of view and the product may vary from cell passage to cell passage. The use of an immortalising gene that will not generate a transformed cell phenotype or otherwise influence the stem cell's biological potency or safety but otherwise enhance the cell's industrial scalability and stabilise the karyotype is highly desirable.

Over the past 10 years increasing information has been emerging about the role of myc oncogenes in normal and cell proliferation, differentiation and apoptosis. To maintain cell proliferation Myc and Max proteins dimerise and translocate to the cell nucleus where they serve as transcription factors. Recently Coller et al., [PROCEEDINGS OF THE NATIONAL ACADEMY OF SCIENCES, 2000; 97:3260-3265] identified 27 genes that were induced, and 9 genes that were repressed by activation of c-myc (cellular myc) in primary human blastocysts. Induced targets included cell cycle genes (e.g. G1 cyclin D2) required to maintain division, and pro-apoptotic genes (e.g. TRAP1) involved in cell death, while repressed targets included genes encoding extra cellular matrix and cytoskeletal proteins, indicating a role for myc in cell adhesion and structure. A recent report has shown that a v-myc (viral myc)-immortalised murine neural stem cell line is able to promote the regeneration of damaged neurons in a Parkinson's disease animal model and promote functional recovery [Ourednik et al., NATURE BIOTECHNOLOGY 20 (11): 1103-1110 NOVEMBER 2002].

The ability of c-myc to maintain cell proliferation makes it a prime candidate for stem cell immortalisation, provided that cell division can be regulated in vivo. For therapeutic use of myc-immortalised cells, a preferred embodiment would permit control over the function of the Myc protein, such that the immortalising protein was not functional after transplanting the cells. This would reduce the risk of overgrowth or tumour formation by the transplanted cells. A preferred conditional form of Myc is a fusion between Myc and the hormone-binding domain of a modified estrogen receptor [Littlewood, et al., NUCLEIC ACIDS RESEARCH, 1995; 23, 1686-1690].

SUMMARY OF THE INVENTION

The present invention is based on the development of cell lines that have favourable characteristics making them useful in transplantation therapy.

According to a first aspect of the present invention, an isolated cell is obtainable from any of the cell lines having the ECACC Accession Nos. 04091601, 04092302 and 04110301.

According to a second aspect of the present invention, a cell identified above, is used in therapy.

According to a third aspect of the present invention, a cell identified above is used in the manufacture of a medicament for the treatment of a disorder associated with loss of our damage to brain cells.

We have generated neural stem cell lines using the regulateable myc immortalising gene, modified to produce a fusion protein of Myc and the hormone binding domain of a modified estrogen receptor. The fusion protein is selectively activated by the synthetic hormone 4-hydroxy tamoxifen (4-OHT). Using a regulateable immortalising gene allows us to maximise conditions for unrestricted cell growth and expansion in culture whilst enabling the cells to terminally differentiate in the absence of 4-OHT when transplanted.

DESCRIPTION OF THE DRAWINGS

The invention is illustrated with reference to the accompanying drawings wherein.

DESCRIPTION OF THE INVENTION

Figure 1:
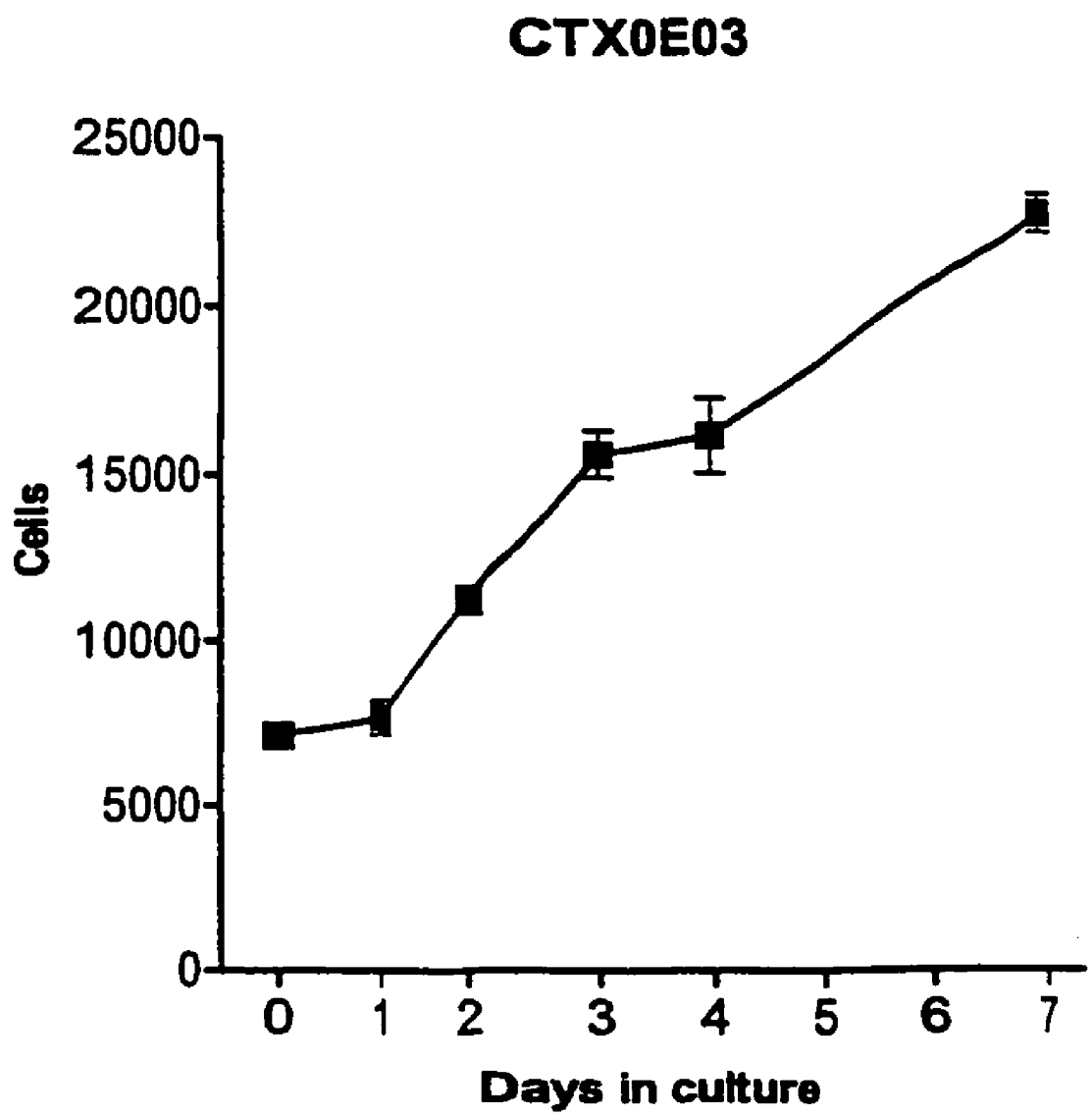
FIG. 1 is a graph showing the growth characteristics of the cell line designated CTXOE03.

The present invention discloses the preparation of cells that are suitable for transplantation therapy and which are immortal up to the time of transplantation.

The cells are modified with the incorporation of a conditional form of MYC oncogene which is controlled by the oestrogen receptor.

The recombinant cells of the invention have use in therapy. In particular, the cells of the invention may be used in the treatment of brain damage. The brain damage may be caused by a degenerative disease or by trauma or hypoxia. In a preferred embodiment, the cells are used in the treatment of Huntington's disease or Alzheimer's disease.

The cells of the invention may be used in a screening assay to identify biological or chemical agents that are of potential use in cell differentiation or which play a role in neural cell development. Screening assays may also be performed to identify agents that have a possible beneficial effect in the treatment of a neurological disease or disorder. The assays are performed by contacting the agent with a culture of one or more of the cells of the invention, and determining whether the agent has an effect on the cell. The assays may be performed in suspension culture, or with adherent cells attached to a substrate surface. The effect may be the ability of the agent to influence differentiation of the cells or the cells' growth characteristics. Alternatively, the agent may be a potential drug and the screening assay is performed to study the toxicology of the agent on the cells.

Methods for the preparation of formulations for delivery to a patient will be apparent to the skilled person. Suitable excipients, diluents etc., will again be apparent based on current practice in preparing cell-based therapies. The amount of cells required for delivery will vary depending on the form of treatment, the severity of the disease/damage, and the need for applying multiple doses over a treatment period. However, the skilled person can readily determine the appropriate treatment based on existing cell transplantation therapies.

The cell lines will now be described in further detail. The cell lines have been deposited at the European Collection of Animal Cultures, Vaccine Research and Production Laboratories, Public Health Laboratory Services, Porton Down, Salisbury, Wiltshire, SP40 JG, UK. The Accession numbers and dates of deposit are as follows:

| Cell Line | Deposit Date | ECACC Accession Number |
|---|---|---|
| CTX-OE03 | Sep. 16, 2004 | 04091601 |
| STROC05 | Nov. 4, 2004 | 04110301 |
| HPCOA07 | Sep. 23, 2004 | 04092302 |

(1) Derivation and Provenance of the Cell Line CTX0E03

Cell Line Summary

A c-MycER$^{TAM}$ transduced human neural stem cell line was derived from 12 week fetal cortex. The line was maintained on laminin coated culture flasks using defined serum-free "Reduced Modified Media" (composition to be described below) in the presence of bFGF, EGF and 4-hydroxy tamoxifen. In routine culture the cell line has a doubling time of around 2-3 days.

In growth medium the cells are nestin positive beta-III tubulin negative with a low percentage of GFAP positive cells. Following differentiation for 7 days there is up-regulation of beta III tubulin expression and acquisition of a neuronal morphology. A low level background of GFAP expression is maintained following differentiation.

Following differentiation there is no expression of MHC class I or class II antigens.

Molecular phenotyping by RT-PCR has confirmed the cells to be mycER positive and nestin positive. In addition a range of neural development genes have been identified as expressed.

This cell line is genetically normal, male XY karyotype, at passage 31 (over 100 population doublings). The cell line is clonal by Southern blot and the genome integration site has been identified within chromosome 13. No known genes are disrupted by this insertion.

Maternal serology indicates the donor to be free from adventitious infections, although a history of prior cytomegalovirus infection was found (CMV ab IgG positive, IgM negative).

pLNC-myc-ER$^{TAM}$

In order to generate a myc-ER driven by a strong promoter the mycER$^{TAM}$ transgene was further cloned into the retroviral vector pLNCX-2 (clontech) which contains a cytomegalovirus promoter (CMV) and a neomycine resistance gene. Plasmid DNA pBabe-puro-myc-ER$^{TAM}$ was amplified as above. Myc-ER$^{TAM}$ sequence in pBabe-puro-myc-ER$^{TAM}$ was excised by restriction enzyme EcoR I. A 2.3 kb fragment of myc-ER$^{TAM}$ was isolated and ligated to Stu I site of pLNCX-2 retroviral vector by blunt-end ligation to generate pLNC-myc-ER$^{TAM}$. The orientation of myc-ERTAM gene in pLNC-myc-ER$^{TAM}$ is determined by restriction digestion with BamH I, Xho I and Bgl II Stock plasmid DNA pLNC-myc-ER$^{TAM}$ was amplified by "Maxi-Prep".

Generation of TEFLY-A Producer Lines

The TEFLY-A and TEFLY-RD virus packaging cell lines (Obtained under licence from CRC UK; U.S. Pat. No. 6,165, 715; GMP Cell Bank stocks held by Genethon, Evry, France) were used to produce MMLV based retroviruses. The cell lines retain the gag, pol and env, genes whereas the viral genome is replaced by the engineered transgene of choice in a retroviral plasmid. TEFLY-RD is used to package virus with restricted infectivity including the TEFLY-A lines. TEFLY-A is used to package/generate amphotropic virus with broad spectrum infectivity for mammalian cells.

pLNC-mvcER$^{TAM}$ Virus

TEFLY-RD producer cells were revived from frozen stocks and new seed stocks established. From expanded stocks, 1.5 million cells were seeded into a 10 cm dish and transfected with 12 μg of pLNC-mycER$^{TAM}$ plasmid using Fugene-6 by standard procedures. Fresh TE-media was put on the transfected cells overnight and packaged virus was harvested from the cells the next morning. This transient virus production was used to infect TEFLY-A producer cells.

Newly acquired TEFLY-A producer cells (TEFLY-A Lot 97-8-02A) were revived from frozen stock and seed stocks established. From the seed stocks, cells were revived, plated out, and infected with supernatant from TEFLY-RD containing pLNC-mycER$^{TAM}$ packaged virus, in the presence of 8 µg/ml polybrene. Infected TEFLY-A producer cells were expanded in culture for 2-3 weeks in the presence of neomycin (G418/Geneticin) to generate a selected (by antibiotic resistance) bulk population of mycER$^{TAM}$ virus producer cells. This bulk population was plated at low density to isolate individual clones. Sixty four clones were isolated by ring cloning and passaged into 24 well plate (1 clone/well). Individual TEFLY-A clones were expanded up to T25 culture flasks at which point cells were prepared for viral harvest over 8 h in fresh TE media. Virus was titred against Te671 cells by serial dilution of the collected media in the presence of 8 µg polybrene. A clone with apparent titres of >$10^6$ cfu/ml was expanded to generate a working stock of 40×1 ml aliquots of 5×$10^6$ cells. Viral stocks collected in "Reduced Modified Media" and "Human Media" were generated for retroviral transduction of primary cell cultures.

Reduced Modified Media

DMEM:F12 supplemented with the components listed below.
  Human Serum Albumin 0.03%.
  Transferrin, Human 100 µg/ml.
  Putrescine Dihydrochloride 16.2 µg/ml.
  Insulin, Human recombinant 5 µg/ml.
  Progesterone 60 ng/ml.
  L-Glutamine 2 mM.
  Sodium Selenite (selenium) 40 ng/ml.
  Plus basic Fibroblast Growth Factor (10 ng/ml) and epidermal growth factor (20 ng/ml) for cell expansion.

Cell Line Derivation

CTXOEO3 was derived under Quality Assured conditions suitable for progressing designated lines for clinical use. As source material, human neural stem cells were isolated post mortem from the cortex of a 12-week gestation foetus (GS031) by enzymatic digestion with trypsin in combination with mechanical trituration. Once established in culture foetal neural cells were infected with amphotropic retrovirus encoding the c-MycER$^{TAMTAM}$ oncogene, and a range of clonal and mixed population cell lines isolated.

All lines in this series were derived on laminin coated culture-ware and using serum free Reduced Modified Media (RMM) comprising DMEM: F12 base media, plus designated supplements as described above and growth factors (bFGF and EGF, as described above).

Growth Characteristics

Under routine culture conditions cells are expanded from frozen stocks, usually 2-4 million cells in T180 culture flasks. After several media changes the cells are passaged when sub-confluent. From process records, population-doubling times for CTXOE03 have been estimated at 3-4 days. This doubling time is slower than for log phase growth and also includes cell loss during the process of subculture.

As a more representative assessment of log phase growth for CTX0E03, a cell proliferation assay was set up using the Cyquant fluorescent dye (Molecular Probes, Invitrogen Inc.). Cell number is measured using a Tecan Magellan fluorescence plate reader; ex 480 nm; em 520 nm.

CTX0E03 cells were passaged, resuspended in RMM plus growth factors and seeded on laminin coated 96 well strip-well plates at 4000 cells/well. A time course study was carried out by removing strips from the plate, removing the media and freezing the cells at −70° C. The media was replaced on the remaining strips (RMM/HM+GFs+4OHT). Each subsequent day media was removed from the next two strips on the plate and frozen at −70° C. At the end of the time course all the frozen strips were put back together on the plate and analysed with the Cyquant assay. Briefly cells are lysed in lysis buffer then Cyquant reagent added and placed in dark for 5 min. A 150 ul sample of each well was then transferred to black, Optilux plates for reading on a Tecan Magellan plate reader. Data was exported to a spreadsheet for numerical averaging and further exported to GraphPad Prism for analysis. The results are shown in FIG. 1.

Conditionality of C-myc Growth Promoting Protein

Figure 2:
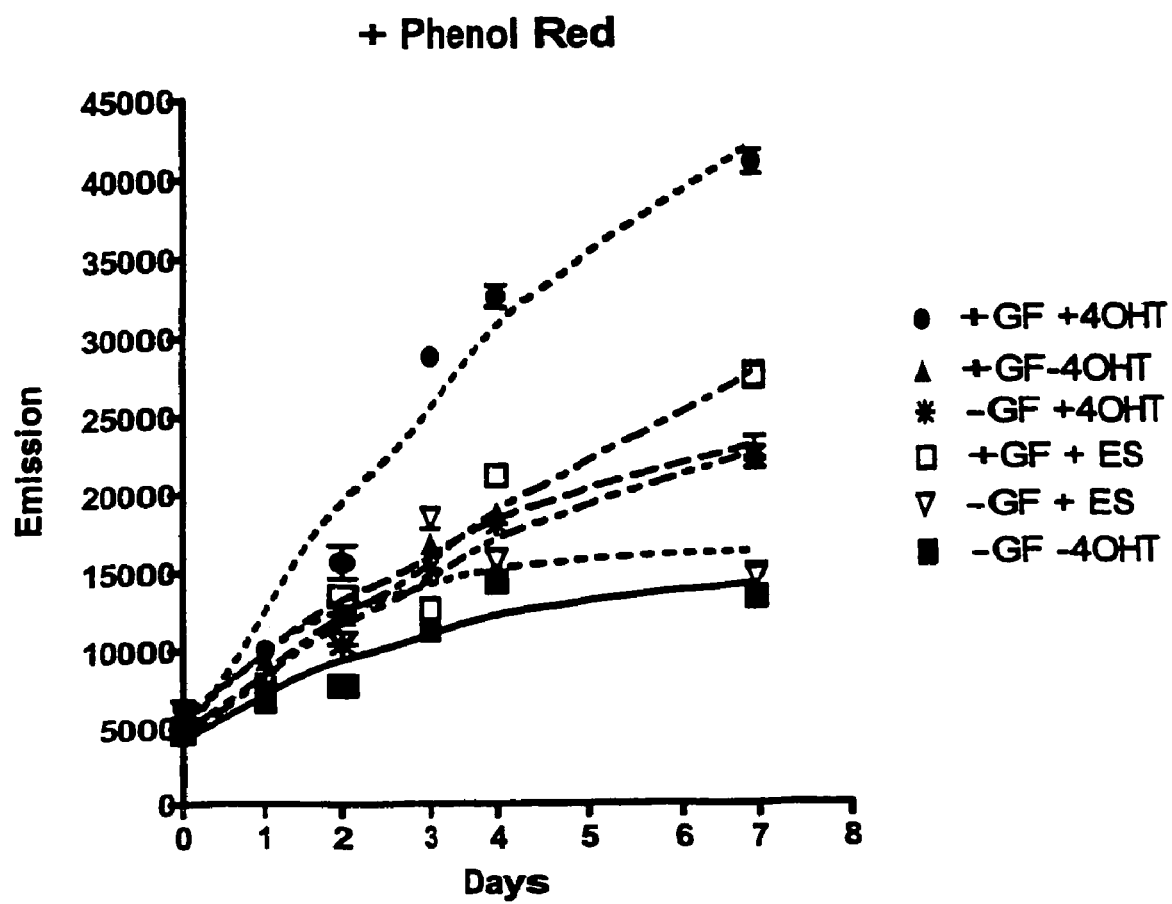
FIG. 2 is a graph showing cell proliferation of the cell line CTXOE03 supplemented with growth factors.

Several studies have been undertaken to consistently demonstrate 4-hydroxytamoxifen conditionality of the c-mycER. Cell growth in the presence or absence of growth factors was enhanced by the application of 4-hydroxy-tamoxifen in the culture media. This effect was not mimicked by beta-estradiol indicating the selective mutation of the estrogen receptor is functionally maintained. The results are shown in FIG. 2.

Phenotype.

The phenotype of the CTX0E03 has been profiled using immunocytochemistry to stain for the neural stem cell marker nestin and to stain for mature markers of differentiation, beta-III tubulin (neuronal) and GFAP (astrocytic).

An assay was established to profile CTXOE3 phenotype in the presence and absence of growth factors plus 4-OHT. Cells were passaged from routine culture and seeded in 96 well tissue culture plates at 4000 cells/well. Two plates were set up. After 3 days one plate of cells in growth media plus 4-OHT was fixed in 4% paraformaldehyde whilst growth factors and 4OHT were removed in the other plate. After a further 5 days without growth factors the second "differentiated" plate of cells was fixed in the same manner. This assay was repeated several times.

Differentiation ICC Images

Cells were fixed in 4% paraformaldehyde for 15 min at room temperature, washed with PBS and permeabilized with 0.1% Triton X100/PBS for 15 minutes. Non-specific binding was then blocked with 10% Normal Goat Serum (NGS) in PBS for 1 hour at room temperature. Cells were then probed with antibodies to Nestin (1:200 Chemicon MAB 5326), Beta-III Tubulin (1:500; Sigma) and GFAP (1:5000; DAKO) at room temperature overnight. After washing with PBS, they were then processed with filtered Alexa Goat α Mouse 488 (1:200; Molecular Probes) and Alexa Goat α Rabbit 568 (1:2500; Molecular Probes) dissolved in 1% NGS/PBS for 1 hour at room temperature. They were then washed with PBS and counterstained with 1 µg/ml Hoechst 33342 (Sigma) for 2 mins before being analysed on a fluorescent microscope.

The results showed down-regulation of nestin and up-regulation of the neuronal marker beta-III tubulin indicating that in the absence of growth factors and 4-OHT for 5 days the cells have differentiated to a more mature neuronal phenotype. There was a background of GFAP (astrocytic) staining which stayed more or less constant.

MHC Class I & II

The expression of MHC antigens on cell lines may contribute to susceptibility of cells to rejection by the host. We have profiled the expression of MHC class I and II on control and differentiated (growth factor withdrawal for 14 days) CTX0E03 cells. Cells were fixed in 4% paraformaldehyde at room temperature then in methanol at −20° C. for 20 mins. After blocking with normal goat serum primary antibody was added at 1:100 dilution; [Class I, HLA-ABC #7855 (AbCam) or Class II, HLA-DR #7856 (AbCam)]. CTX 0E03 had no class II expression in contrast to a control cell line 0E33. Similarly CTX0E03 was negative for Class I expression in both undifferentiated and differentiated cells.

Genetic Stability

G-banding Karyotype Analysis

Karyotyping was carried out as follows:

From T25 flask cultures, 70-80% confluent cells were washed, stained with Bromodeoxyuridine, treated with Colcimid and subjected to hypotonic lysis. Samples were then fixed in methanol: glacial acetic acid [3:1] and stored at −20° C. Samples were then analysed and shown to have a normal karyotype. G-Banding analysis was conducted approximately every ten passages from Passage 5 to Passage 40, yielding normal diploid chromosomes with no abnormalities detected.

Clonality/Southern Blot for CTX-OE-03

Southern transfer and hybridisation can be used to study the clonality and integration of the retrovirally-itransduced genetic construct within the genome of cell lines by mapping with a probe specific for the construct. Genomic DNA (GDNA) is first digested with restriction enzyme and the resulting fragments are separated according to size by agarose gel electrophoresis. The DNA is then denatured in situ and transferred from the gel to a solid support (nitrocellulose membrane). The DNA attached to the membrane is hybridised to a $^{32}P$ labelled DNA probe against a specific portion of the construct and bands complementary to the probe are located by autoradiography. If the cell lines are clonal and with only a single integration site, only one band of specific size will be present, if not clonal then two or more bands corresponding to different integration sites will be present.

Results

The Southern blot for CTX-OE-03 shows this cell line is clonal with a single band present at 6 kb.

Genome Integration Site

Integration of retroviral DNA into the target cell genome is primarily a random event. Inverse PCR has been widely used to detect the integration site of retroviral transgenes in many cell lines (Schmidt et al., ANNALS OF THE NEW YORK ACADEMY OF SCIENCES. 2001. 938:146-155). It is also a powerful tool to identify clonality. Here inverse PCR was used to identify the pLNC-myc-ER$^{TAM}$ integration site in CTX-0E03 line.

Genomic DNA was isolated from CTX-0E03 (5×10$^6$ cells), and digested over-night with Hind III. The digested DNA was ligated by using T4 DNA ligase to form circular DNA. Two pairs of primers targeting a specific region of the mycER gene were used to PCR the whole circular DNA. Using this approach the flanking sequence of the c-MycER insertion is recovered. A ~6 kb fragment was detected in 1.2% agrose gel that contains the flanking regions corresponding to the genome integration site.

Safety

Maternal serology indicate the donor to be free from the following infections;

| HIV 1&2 Abs | Not detected |
| CMV IgM | Not detected |
| Hep C Ab | Not detected |

-continued

| Hep B surface Ag | Not detected |
| Toxoplasma IgG | Not detected |
| Anti-HTLV-I/II EIA | negative |
| Anti-HTLV-I GPA | negative |
| VDRL Slide Test./TPHA test | Syphilis negative |

Positive serology was found as follows.

| CMV IgG | detected |

(II) Derivation and Provenance of the C-MycER$^{TAM}$ Immortalised Cell Line STR0C05

Summary

A c-MycER$^{TAM}$ transduced-neural stem cell line was derived from 12 week fetal striatum. The line is maintained on laminin coated culture flasks using defined serum free "Human Media" in the presence of bFGF, EGF and 4-hydroxy tamoxifen. In routine culture the cell line has a doubling time of 3-4 days although in short term culture a doubling time of 20-30 h was seen.

In growth medium the cells are nestin-positive, beta-III tubulin-negative with a low percentage of GFAP positive cells. Following differentiation for 7 days there is down regulation of nestin with low-level expression of beta III tubulin and strong expression of GFAP suggesting that the cell line becomes predominantly astrocytic.

This cell line is genetically normal, male XY, and stable over 50 population doublings.

Introduction

The lines described here were derived under Quality Assured conditions suitable for progressing designated lines for clinical use. As source material, human neural stem cells were isolated post mortem from the striatum of a 12-week gestation fetus GS006 by enzymatic digestion with trypsin in combination with mechanical trituration. Once established in culture these primary neural cells were transformed by retroviral transduction with the c-MycER$^{TAM}$ oncogene (as described for the CTXOEO3 cell line above) and a range of clonal and mixed population cell lines isolated. All lines in this series were derived on laminin coated culture-ware and using Human Media (HM); DMEM:F12 plus designated supplements as described below.

Human Media (HM)

DMEM:F12 supplemented with the components listed below.

| Human Serum Albumin | 0.03%. |
| Transferrin, Human | 100 µg/ml. |
| Putrescine Dihydrochloride | 16.2 µg/ml. |
| Insulin, Human recombinant | 5 µg/ml. |
| L-Thyroxine (T4) | 400 ng/ml. |
| Tri-Iodo-Thyronine (T3) | 337 ng/ml. |
| Progesterone | 60 ng/ml. |
| L-Glutamine | 2 mM. |
| Sodium Selenite (selenium) | 40 ng/ml. |
| Heparin, sodium salt | 10 Units/ml. |
| Corticosterone | 40 ng/ml. |

Plus basic Fibroblast Growth Factor (10 ng/ml) and epidermal growth factor (20 ng/ml) for cell expansion.

Growth Characteristics

Under routine culture conditions cells are expanded from frozen stocks, usually 2-4 million cells in T180 culture flasks After several media changes the cells are passaged when confluent. From process records, population doubling times for STR0C05 have been estimated at 3-4 days as shown on the graph below. This doubling time is slower than for log phase growth and also includes cell loss during the passaging.

As a more representative assessment of log phase growth for STR0C05, a cell proliferation assay was set up using the Cyquant fluorescent dye (Molecular Probes). Cell number is measured using a Tecan Magellan fluorescence plate reader; ex. 480 nm; em 520 nm.

STR0C05 cells were passaged, resuspended in HM plus growth factors and seeded on laminin coated 96 well stripwell plates at 5000 cells/well. A time course study was carried out by removing strips from the plate on a daily basis, n=16 wells per time point, removing the media and freezing the cells at −70° C.

At the end of the time course all the frozen strips were put back together on the plate and analysed with the Cyquant assay. Briefly cells are lysed in lysis buffer then Cyquant reagent added and placed in dark for 5 minutes. A 150 ul sample of each well was then transferred to black, Optilux plates for reading on a Tecan Magellan plate reader. Data was exported to an Excel spreadsheet for numerical averaging and further exported to GraphPad Prism for analysis.

The results showed that the cells grew steadily over 7 days with an estimated doubling time of 20-30 hours.

Phenotype

The phenotype of the STR0C05 has been profiled using immunocytochemistry to stain for the neural stem cell marker nestin and to stain for mature markers of differentiation, beta-III tubulin (neuronal) and GFAP (astrocytic).

STR0C05 phenotype was determined in the presence and absence of growth factors plus 4-OHT. Cells were originally sourced from STR0C05 working stock. Cells were passaged and seeded in 96 well plates.

Cells were fixed in 4% paraformaldehyde for 15 minutes at room temperature, washed with PBS and permeabilisd with 0.1% Triton X100/PBS for 15 minutes. Non-specific binding was then blocked with 10% Normal Goat Serum (NGS) in PBS for 1 hour at room temperature. Cells were then probed with antibodies to Nestin (1:200, Chemicon), Beta-III Tubulin (1:500; Sigma) and GFAP (1:5000; DAKO) at room temperature overnight. After washing with PBS, they were then processed with filtered Alexa Goat a Mouse 488 (1:200; Molecular Probes) and Alexa Goat α Rabbit 568 (1:2500; Molecular Probes) dissolved in 1% NGS/PBS for 1 hour at room temperature. They were then washed with PBS and counterstained with Hoechst 33342 (Sigma) for 2 minutes before being analysed on a fluorescent microscope.

Removal of growth factors and 4-OHT from the medium induces a morphological and phenotypic change in the cells that is accompanied by down regulation of nestin. Specifically a small proportion of the cells become positive for the neuronal marker beta-III tubulin and acquire a neuronal morphology with rounded cell bodies extending into dendritic/axonal outgrowths. The more dominant phenotypic change however is the up-regulation of GFAP suggesting a predominance of an astrocytic lineage.

Clonality

Southern Blot for STR0C05

To date in two separate experiments there is no evidence of probe hybridisation in contrast to clear bands seen with other cell lines.

(III) Derivation and Provenance of the C-mycER$^{TAM}$ Immortalised Cell Line HPC0A07

Summary

An immortalised neural stem cell line was derived from 12-week fetal hippocampus. The line is maintained on laminin coated culture flasks using defined serum free "Reduced Modified Media" in the presence of bFGF, EGF and 4-hydroxytamoxifen. In routine culture the cell line has a doubling time of around 2 days; in short term culture a doubling time of 20-30 hours is also seen.

In growth medium the cells are nestin positive beta-III tubulin negative with a low percentage of GFAP positive cells. Following differentiation for 7 days there is up-regulation of beta III tubulin expression and acquisition of a neuronal morphology. A low level background of GFAP expression is maintained following differentiation.

Following differentiation there is up-regulation of MHC class II antigens but not Class I.

Molecular phenotyping by RT-PCR has confirmed the cells to be mycER positive and nestin positive. In addition a range of neural development genes have been identified as present.

This cell line is karyotypically normal, female XX, at passage 8 (over 20 population doublings). Later passage data is currently being processed.

Maternal serology indicates the donor to be free from major infections.

Introduction

As source material, human neural stem cells were isolated post mortem from the hippocampus of a 12-week gestation foetus by enzymatic digestion with trypsin in combination with mechanical trituration. Once established in culture foetal neural cells were transformed by retroviral transduction with the mycER$^{TAM}$ oncogene, and a range of clonal and mixed population cell lines isolated.

All lines in this series were derived on laminin coated culture-ware and using serum free media known as Reduced Modified Media (RMM) (see above) for composition comprising DMEM:F12 base media, plus designated supplements.

Growth Characteristics

Under routine culture conditions cells are expanded from frozen stocks, usually 2-4 million cells in T180 culture flasks. After several media changes the cells are passaged when confluent. From process records, population doubling times for HPC0A07 have been estimated at 3-4 days. This doubling time is slower than for log phase growth and also includes cell loss during the passaging Cell Proliferation Assay As a more representative assessment of log phase growth for HPC0A07, a cell proliferation assay was set up using the Cyquant fluorescent dye (Molecular Probes). Cell number is measured using a Tecan Magellan fluorescence plate reader; ex.480 nm; em 520 nm.

HPC0A07 cells were passaged, resuspended in RMM plus growth factors and seeded on laminin coated 96 well stripwell plates at 4000 cells/well. A time course study was carried out by removing strips from the plate, removing the media and freezing the cells at −70° C. The media was replaced on the remaining strips (RMM/HM+GFs+4OHT). Each subsequent day media was removed from the next two strips on the plate and frozen at −70° C.

At the end of the time course all the frozen strips were put back together on the plate and analysed with the cyquant assay. Briefly cells are lysed in lysis buffer then Cyquant reagent added and placed in dark for 5 minutes. A 150 ul sample of each well was then transferred to black, Optilux plates for reading on a Tecan Magellan plate reader.

Figure 3:
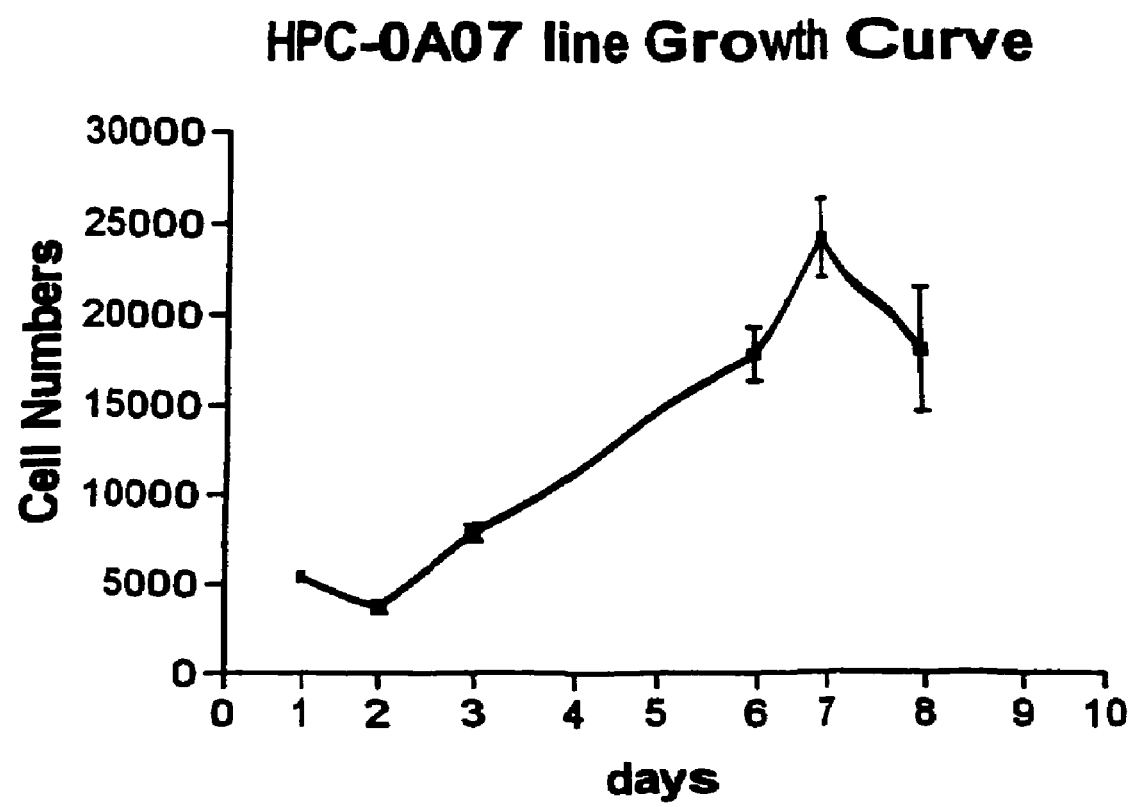
FIG. 3 is a graph showing the growth characteristics of the cell line designated HPC-OA07

The cells expanded over 4-5 days with a doubling time of 1-2 days (as shown in FIG. 3).

Phenotype

The phenotype of the HPC0A07 has been profiled using immunocytochemistry to stain for the neural stem cell marker nestin and to stain for mature markers of differentiation, beta-III tubulin (neuronal) and GFAP (astrocytic).

An experiment was carried out to profile HPC0A07 phenotype in the presence and absence of growth factors plus 4-OHT. Control (undifferentiated) cells and cells grown for 7 days in the absence of growth factors and 4-OHT were fixed in 4% paraformaldehyde and subjected to immunocytochemistry as described.

Cells were fixed in 4% paraformaldehyde for 15 minutes at room temperature, washed with PBS and permeabilizd with 0.1% Triton X100/PBS for 15 minutes. Non-specific binding was then blocked with 10% Normal Goat Serum (NGS) in PBS for 1 hour at room temperature. Cells were then probed with Beta-III Tubulin (1:500; Sigma) and GFAP (1:5000; DAKO) at room temperature overnight. After washing with PBS, they were then processed with filtered Alexa Goat α Mouse 488 (1:200; Molecular Probes) and Alexa Goat α Rabbit 568 (1:2500; Molecular Probes) dissolved in 1% NGS/PBS for 1 hour at room temperature. They were then washed with PBS and counterstained with Hoechst 33342 (Sigma) for 2 minutes before being analysed on a fluorescent microscope.

The images show strong up-regulation of the neuronal marker beta-III tubulin accompanied by morphological changes consistent with neurones. There is a low level of astrocytic cells in both control and differentiated cells as indicated by the GFAP staining.

MHC Class I & II

Cells were set up in laminin coated 96 well plates and expanded in RMM plus growth factors plus 4-OHT. Cells were differentiated for 7 or 14 days by removing growth factors and 4OHT from the medium.

MHC class I is not expressed in control or differentiated cells after 7 or 14 days. By contrast MHC II is strongly expressed in differentiated cells especially at 14 days. Undifferentiated cells show no MHCII expression.

Genetic Stability

Karyotyping Analysis

The cells were shown to have a normal female karyotype.

Clonality

Southern blot for HPC0A07 shows a single band at 5 kb suggesting that this cell line is clonal.

Safety

Maternal serology from GS011 indicates the donor to be free from the following infections;

| | |
|---|---|
| HIV 1&2 Abs | Not detected |
| CMV IgG | Not detected |
| CMV IgM | Not detected |
| Hep C Ab | Not detected |
| Hep B surface Ag | Not detected |
| Toxoplasma IgG | Not detected |
| Anti-HTLV-I/II EIA | negative |
| Anti-HTLV-I GPA | negative |
| VDRL Slide Test/TPHA test | Syphilis negative |

Therapeutic Use of Cells

CTXOEO3 Stem Cell Line Reduces Deficits After MCAo Stroke in Rats.

The aim of this study was to test the efficacy of human neural stem cell lines developed by this invention in promoting functional recovery after middle cerebral artery occlusion in rat, a validated model of embolic stroke in humans.

Two human cell lines, CTXOE03 (n=10) and a cell line with similar phenotype derived from the striatum, STROB05 (n=9), were implanted into cortex and striatum (bilaterally) 3 to 4 weeks after stroke induced by 70 minutes of intraluminal right middle cerebral artery occlusion. There were two vehicle grafted control groups: stroke (n=7) and sham operated (n=11). Six to twelve weeks after grafting, all four groups were tested for bilateral asymmetry, vibrissae-elicited forelimb placing, rotation bias and a spatial learning task before histological investigation of lesion volume, cell distribution and differentiation.

Rats with cell line grafts displayed reduced bilateral asymmetry and amphetamine induced rotation when compared to the stroke control animals. The STROB05 group also displayed reduced dysfunction in the forelimb placing test compared to the stroke controls. These improvements did not reach sham control levels. Neither of the cell line grafted groups showed reduced dysfunction in the spatial learning task or differences in lesion volume compared to the stroke alone group. STROB05 grafts survived well, but grafted cells were seen in a smaller number of the rats in the CTXOE03 group. Neither cell line showed neuronal differentiation at 14 weeks after grafting. In conclusion, both of the grafted cell lines promoted behavioural recovery over the course of the study.

Middle cerebral artery occlusion (MCAo) produces behavioural deficits that are evident using neurological, sensorimotor, and spatial memory tests. There is spontaneous resolution of many deficits in animals by 30 days after occlusion paralleling recovery seen in patients over months of recovery after stroke. We used tests in this study that are robust in identifying long-term deficits, ensuring that improvements reflect true recovery, not reduced stroke damage or accelerated rehabilitation.

Materials and Methods

MCAo

Male Sprague-Dawley rats (Charles Rivers) were group housed (12:12 hours light dark) for 7 days prior to occlusion, with food available ad libitum. Procedures complied with the UK Animals (Scientific) Procedures Act (1986) and the Ethical Review Process of ReNeuron Ltd.

Animals were prepared for surgery (320-370 g) and subjected to 70 minutes of middle cerebral artery occlusion using a 3-0 prolene filament coated with silicone (Halford's UK). Halothane (in 70% NO2/30% $O_2$) anaesthesia was used for insertion and removal of the filament, with temperatures held at 37±1° C. by rectal probe and heating pad. Once the filament was inserted (~20 mm), animals were allowed to recover from anaesthesia. At 60 minutes into occlusion, animals were evaluated for behavioural dysfunction (forelimb flexion and contralateral circling behaviour). Animals that did not demonstrate dysfunction were removed from the study. At the end of the occlusion period, the animals were re-anaesthetized and the filament partially withdrawn to clear the base of the MCA. The wound was closed, saline administered, and the animals placed in a heated chamber for 2 hours. Animals were put into post-operative care. Sham MCAo animals underwent anaesthesia and filament placement of 5-6 mm.

For 2 days after MCAo, all animals had rehydration therapy (Duphalyte [Fort Dodge]) in saline, 5 mls 50:50 mixture), were scored for neurological dysfunction and weighed (further rehydration therapy was administered as necessary with continued scoring and weighing). Once pre-occlusion body weight was reached, animals were tested on the tape removal and rotameter tasks (see below) to provide baseline scores for the test battery and to allow for balancing experimental groups. Rats were assigned to either sham, vehicle infusion of N-acetyl-L-cysteine (NAC), STROB05 grafting or CTXOE03 grafting.

The STROB05 and CTXOE03 cell lines were harvested and suspended at a concentration of ~50,000 cells/ul in NAC (Sigma). Cells were prepared twice during the days of grafting. Cell viability was recorded both at the beginning of transplantation and after grafting via trypan blue exclusion (Sigma). Cell viability was high (over 85%) before and after grafting sessions. Control MCAO and sham animals both had infusions of the grafting vehicle, NAC (Sigma) in Hanks' balanced salt solution (Gibco).

At 3-4 weeks after occlusion, animals were injected with cyclosporin A (CSA)(Sandimmun, 10 mg/kg SC: Sandoz) in Cremaphore el (Sigma), then grafted 24 hours later. Animals were pre-anaesthetized with medetomidine hydrochloride (Domitor, 0.5 mg/kg, i.p. Pfizer), then anaesthetized with ketamine hydrochloride (Vetalar 80 mg/kg, i.p., Pharmacia Upjohn). After preparation, animals were placed into stereotaxic frames, the scalp incised, skull exposed and bregma located. Grafts were deposited using a flat tipped 10 μl Hamilton syringe at 4 sites, ipsilateral and contralateral to the occluded hemisphere at the following coordinates relative to bregma: (+0.7 mm AP, ±3.0 mmLat, −5.5, −2.0 mm Vert; −0.3 mmAP, ±0.35 mm Lat, −5.5, −2.0 mm Vert). Cells were injected at a rate of 1 ul/minute and the syringe kept in place for another minute to reduce reflux. Once all cells were injected (400,000/animal), the wounds were sutured shut, the animal given saline rehydration, and anti-inflammatory treatment; (methylprednisilone; medrone 20 mg/kg sc, Pharmacia Upjohn) and CSA. Anaesthesia was reversed with atipamezole hydrochloride (antisedan, 0.1 mg/kg, Pfizer) and analgesic was provided with bupranorphine hydrochloride (vetergesic, 0.1 mg/kg, Alstoe Animal Health). Once animals had recovered fully from anaesthesia, they were placed into post-operative care, including rehydration therapy for 2 days after surgery. Animals received post-operative immunosuppresion treatment with medrone daily for 20 days, and CSA thrice weekly over the course of the study.

At 6 weeks after grafting, animals began the sensori-motor test battery. Animals had 1 forelimb placing test per week with 3 trials per session, 2 sticky tape tests with 2 trials per session, and 1 half hour rotameter test per week, alternating saline and amphetamine trials. At 12 weeks post-grafting, the sensori-motor testing ended and the animals were tested for acquisition in the Morris water maze for 10 working days.

Vibrissae-elicited Forelimb Placing Test

Animals were held with one forelimb free and moved toward a tabletop. When the vibrissae brush the table, the ipsilateral paw is placed onto the tabletop. The number of appropriate limb placements after 3 brushes per side was recorded.

Bilateral Asymmetry

The bilateral asymmetry test of sensorimotor dysfunction measured the disparity in time taken to contact and remove sticky tape strips (~1×6 cm) wrapped around the affected and unaffected forepaws for 300 seconds Rotameter The rotameter (TSE GmbH) measured motor rotation asymmetry in response to amphetamine (2.5 mg/kg sc, Sigma) or saline administration. Rotation bias was calculated, as the number of anti-clockwise turns divided by the total number of turns in both directions.

Histological Evaluation

Animals were overdosed with pentobarbitone (Animalcare), flushed transcardially with heparinized saline, and perfused with 4% paraformaldehyde in 0.2 mol/L PBS. Brains were cryoprotected by 30% sucrose and cut by sliding cryomicrotome (Frigomobile:Leica) into 50 μm sections. Lesion volume was calculated in every $20^{th}$ section by Simpson's rule with the use of digital microscope images analysed by Image Pro Plus (Media Cybernetics). Transplanted cells were identified by the use of antibodies raised against human nuclear protein (HuNuc—Chemicon Inc). Differentiation of transplanted cells was determined by colocalizing phenotypic markers, neurofilament and KI-67 with the human protein. Primary antibodies were incubated overnight before the fluorescent anti-mouse or anti-rabbit secondary antibody was applied for 1 hour.

Statistical Analyses

Results for the bilateral asymmetry tests were analysed by 2-way ANOVA (Prism) with groups as the between-subjects factor and trials/days as the within-subjects factor. t-tests were used to analyse prelesion versus postlesion performance in the rotameter test. One-way ANOVAs were used for group differences on the rotameter, whiskers, and lesion volumes. The Bonferroni post hoc test was used to compare groups.

Results

Occluded animals showed gross neurological dysfunction for the first 7 to 14 days after occlusion. This dysfunction was accompanied with mild weight loss (<30%). Dysfunction and weight loss were usually resolved within 14 days after occlusion. Post-hoc analysis determined that weight loss at 7 days post occlusion correlated to final lesion volume when analysing all animals in the study ($r=-0.705$, $p<0.0001$).

Vibrissae-elicited Forelimb Placing Test

There were significant differences in the number of limb placements between the affected and non-affected limbs in all three of the occluded groups ($p<0.0001$). There was no difference in limb placements within the sham group. There was a significant difference in placements of the affected limb between the sham group and the occluded groups ($p<0.001$ all groups). There was also a significant difference in placements of the affected limb between the STROB05 grafted and the stroke control ($p<0.01$) and CTXOE03 ($p<0.001$) grafted groups. The STROB05 group did not reach the levels of placements seen in the sham group for the affected limb.

Bilateral Asymmetry Task

Contact; There were significant differences in the time to contact the tape on the affected (left) paw with the stroke control treated animals taking longer than the sham, STROB05 and CTXOE03 grafted groups (p<0.01 all groups, ANOVA). There were also significant differences between groups with the sham animals taking longer than the stroke controls and CTXOE03 groups in contacting the tape on the non-affected paw (p<0.05, ANOVA).

Removal; There were significant differences between groups with the NAC treated animals taking longer than the sham, STROB05, and CTXOE03 grafted groups in removing the tape from the affected (left) paw (p<0.001, all groups ANOVA). There were significant differences between groups with the sham animals taking longer than the NAC, STROB05, and CTXOE03 grafted groups in removing the tape from the non-affected (right) paw (p<0.0001 all groups, 2-way ANOVA).

Rotameter

Saline: Asymmetry of spontaneous rotations following saline administration was significantly lower in the CTXOE03 and sham groups when compared to the NAC treated group after grafting (p<0.05). There was a significant reduction in the bias of spontaneous rotations after grafting when compared to pre-grafting performance in the STROB05 (p<0.01) and CTXOE 03 (p<0.05) groups.

Amphetamine: Asymmetry of amphetamine induced rotations, ipsilateral to the lesion was reduced in the cell line grafted and sham animals when compared to the occluded NAC treated animals after grafting (p<0.001). There was still a significant difference between the sham and cell line grafted groups with the grafted groups having a higher percentage of counter-clockwise rotations (p<0.01). There was a significant reduction in amphetamine-induced asymmetry after grafting when compared to pre-grafting performance in the STROB05 (p<0.05) and CTXOE03 (p<0.01) groups.

Lesion Volumes; There were significant differences in the volume of damaged tissue between the sham (24.0 $\pm$~5.1 mm$^3$) and the NAC (220.6 $\pm$~32.5 mm$^3$), STROB05 (250.0 $\pm$~37.0 mm$^3$) and CTXOE03 (214.2 $\pm$~36.5 mm$^3$) groups (p<0.001 all groups, ANOVA), with no differences between the NAC and grafted groups. Damage typically occurred throughout the sensory and motor cortices and striatum. Thalamic atrophy indicated secondary degeneration, however, no gross damage to the hippocampus was apparent.

Immunohistochemistry

Human cells were identified in both the STROB05 and CTXOE03 grafted groups. There was good survival in most of the STROB05 grafted animals (7/9) but CTXOE03 animals had good survival in only 2 of 9 animals. Neither cell line demonstrated differentiation into neurons in any of the animals at long-term survival. The STROB05 cell had some co-localization of human nuclear and KI-67 protein expression (a marker for cell division) in the areas of cavitation outside the parenchyma suggesting that local cues may have promoted cell division. There was good migration in one of the CTXOE03 grafted animals with cells migrating throughout the sections.

STROCO5 and CTXIE03 Stem Cell Lines Reduce Deficits After Quinolinic Acid Lesions of the Sriatum (Modelling Huntington's Disease) in Rats The study aimed to assess effects of human MycER$^{TAM}$ cell lines STROCO5 nd CTXOEO3 in rats with deficits induced by unilateral (left side) quinolinic acid striatal lesions, as a partial model for Huntington's disease (HD).

Quinolinic acid produced selective damage to DARPP 32 positive neurons in the striatum, which was uniform and across groups spared other cell types. These discrete lesions did not result in amphetamine-induced rotation bias or deficits in spatial learning. However deficits were seen in tests of sensorimotor (sticky tape removal times) and motor function (pellet retrieval on the staircase) especially with the right paw. There was a marked lesion effect in elicited reflex responses shown in the body swing and whiskers tests. The STROCO5 grafted group showed significant improvement relative to lesion-only animals in pellet retrieval on the staircase test, in body swing bias and paw placement after whisker stimulation. The CTXOEO3 grafted group showed similar improvements in performance in the body swing bias and paw placement after whisker stimulation. Grafts were visualised long term in about 50% of the grafted rats. These results indicate a potential for repair of a range of motor responses in rats with HD-like loss of medium spiny striatal output neurons.

Materials and Methods

Male Sprague-Dawley rats (Charles Rivers) were group housed (12:12 hours light dark) for 7 days prior to surgery, with food available ad libitum. Procedures complied with the UK Animals (Scientific) Procedures Act (1986) and the Ethical Review Process of ReNeuron Ltd.

Animals were prepared for surgery (mean weight 379 g). For lesions, the rats were anaesthetised with ketamine (Ketalar, 80 mg/kg, Pharmacia and Upjohn Ltd. UK) and medetomidine (Domitor 0.5 mg/kg, Pfizer, UK) reversed after surgery by Atipamezole (Antisedan; Pfizer, UK) and placed in a stereotaxic frame (Kopf, Tujunga Calif.). A homeothermic blanket was used to maintain body heat. Holes were drilled in the skull to allow insertion of a cannula attached by tubing to a 10 ul Hamilton Syringe driven by a pump (Harvard Instruments). The following coordinates (mm) were used, for a left-sided lesion with the skull held in flat position (3.5 mm below the inter aural line).

(1) AP=0.0; L=+3.5; V=−4.5 and (2) AP=+1.2; L=+2.8; V=−4.5

0.08 M quinolininic acid (Sigma, UK) was prepared by weighing out 13.368 mg of quinolinic acid ((2,3-Pyridinedicarboxylic Acid, Sigma UK), adding 0.5 ml of PBS and 10-20 ul of 1 M sodium hydroxide solution, and sonicating until dissolved. PH was checked and adjusted if required, and the solution made up to 1 ml with PBS. 1.0 ul of quinolinic acid was infused over 2 minutes. The cannula was left in place for a further 2 minutes, to allow diffusion of the toxin. Surgery took place over two weeks.

Surgery—Grafting: Rats were anaesthetised and placed in the frame, and the skull sites prepared as for lesioning. A 10 ul flat-tipped Hamilton syringe into the lesion sites at the following coordinates delivered cell suspensions:

1) AP=0.0; L=+3.6; V=−5.5, −4.5 and (2) AP=+1.2; L=+2.8; V=−5.5, −4.5.

2 deposits of 3 ul at a density of 50,000 cells/uil were delivered at each site (i.e. 6 il=300,000 cells/rat) over 3 minutes. The syringe was lowered to the deepest point first and 1.5 ul cells dispensed, before raising the needle to the upper site to deliver the remaining 1.5 ul of suspension. The syringe was slowly withdrawn after waiting for 2 minutes dispersal. resh draws of suspension were taken for each site. Cells were freshly prepared and delivered twice a day (am, pm) to reduce deterioration on the bench.

All rats received immunosuppressive treatments consisting of cyclosporin A (10 mg/kg sc) in Cremophor EL (CSA/CEL) in a ratio of 1:4, starting the day before surgery and continuing for 3 days/week until perfusion. In addition rats were injected daily (20 mg sc) with n-methyl prednisalone (Solumedron) for 2 weeks, starting on the day of surgery.

Final Group sizes were: Lesion and sham graft, N=7, Control, N=9, STROCO5, N=9, CTXOEO3, N=12.

At 6 weeks after grafting, the rats commenced behavioural testing.

Reflex Motor Response Testing:

Body Swing Test (BST). Rats were placed in an open cage facing the experimenter and lifted by the base of the tail above floor level for 10 seconds. Twists defined as distinct kicks in which hindlimbs crossed the midline to the animals' left or right were recorded. Preferably two experimenters were used, one to hold and one to record. This provided inter-experimenter reliability. If the rat twisted first towards the lesioned side (left in this case) a score of 1-3 was recorded for the intensity of the swing. A contralateral swing was recorded as zero score. Inter-rater reliability for scores was relatively low, so this qualitative measure was not used in the final analysis of results, which used % left swings, to measure bias.

Each session (block) consisted of 3 10-second lifts. One session was given in the week after lesion surgery to assess the lesion, and 6 blocks were given at weekly intervals over weeks 6-12 after grafting to assess graft effects.

Paw placement in response to vibrissae stimulation.

Rats were held with one forepaw free and the other restrained, and whiskers adjacent to the free paw gently brushed against the side of a table. The rat immediately reached to touch the table. However rats with unilateral damage often failed to place the paw contralateral to the damage on the tabletop. Each session consisted of three trials on each side, in alternation. Rats were scored 1 for reaching and 0 for failure to respond within a 5 second period. Four sessions were given at the end of behavioural testing, weeks 9-10 after grafting.

Sensorimotor Dysfunction Testing:

Staircase Test:

The apparatus consists of an entry chamber giving access to a platform flanked by two seven-step staircases, with a hollow for pellets on each step. Rats climb onto the platform to reach pellets (2 Coco Pops; Kellogs Ltd.) on each step. A narrow lip on the edge of the platform prevented rats from scraping up the pellets, for successful retrieval pellets must be grasped and lifted to the mouth, using the right and left forelimb for each side. Rats were given two 5-minute trials per session. Rats were trained before lesioning (2 sessions), tested after lesioning (2 sessions) and after transplantation (4 sessions), over the same period as BAT testing.

Histology

Perfusion and Sectioning:

Rats were transcardially perfused with 4% paraformaldehyde in 0.1 M sodium phosphate buffer (PBS, pH 7.4), brains were removed and stored in fixative at 4° C. overnight, then transferred to 30% sucrose in PBS. 50 µm serial sections were cut on a freezing microtome, collected in sucrose in 24 well culture plates and stored at −20° C. until processing.

Lesion Damage:

Lesions were quantified as the extent of loss of DARPP 32 positive cells throughout the left striatum; both the area of immunoreactivity and the intensity of staining were measured, using c. 8 sections running through the AP axis of the striatum.

Grafted Cell Survival:

Grafted cells were identified by Human Nuclear (HuNuc—Chemicon Inc) staining and counted in serial sections adjacent to those used for lesion evaluation, throughout the grafted striatum. Sections close to the injection site were the chief focus of scrutiny.

Results

Staircase Test

More pellets were retrieved with the left than the right paw ($p<0.05$), across all groups. There was a substantial difference between Groups ($p<0.001$) since lesioned rats retrieved fewer pellets than STROCO5 grafted and control groups ($p<0.01$).

Body Swing Test

Lesioned rats showed substantial bias in twisting to the left throughout the six blocks of post-transplant testing, hence Groups differed in percentage of left swings. ($p<0.001$: see Fig). Hence there was a substantial difference between groups: both the CTXOEO3 and STROCO5 grafted as well as the control groups showed reduced bias (i.e. c. 50% swings to left and right), and differing significantly from lesioned rats ($p<0.01$). In terms of the actual numbers of swings to left and right, an interaction between Groups and side ($p<0.001$ underlines the bias in lesioned, but not control or grafted groups.

Paw Placement in Response to Ipsilateral Vibrissae Stimulation.

Lesioned rats failed to respond consistently to stimulation of whiskers on the right side, although reaches to the tabletop with the left paw were fast and accurate after stimulation on the left side. Control and grafted groups responded to stimulation on both sides. Therefore sides differed significantly ($p<0.001$) and there was a massive interaction between Groups and Sides ($p<0.001$), as well as a substantial difference between Groups ($p<0.001$). Control and STROCO5 and CTXOEO3 grafted groups differed from lesioned rats ($p<0.001$). However, both grafted groups were less responsive than control rats ($p<0.02$) so that they still showed some neglect.

Histological Findings

Lesion Size and Specificity

Lesions were well targeted to the striatum, and involved little tissue loss apart from the absence of DARPP 32 positive cells, and some ventricular enlargement. The area of cell loss averaged 10 mm$^3$ in both lesion-only and grafted groups. There was also no difference in lesion volume/intensity in grafted rats with and without surviving cells.

Graft Survival:

Surviving HuNuc positive cells were seen in 4/9 STROCO5 grafted rats and 5/12 CTXOEO3 grafted rats. Good migration was seen in 75% of animals with grafts. There was no apparent differentiation of long-term surviving grafted cells into neurons.

HPCOAO7 and CTXOEO3 Cell Lines Restore Cognitive Performance After Global Ischaemia (4-Vessel Occlusion)

The experiment aimed to see whether grafts of two regulated human c-MycER$^{TAM}$ stem cell lines would be able to improve spatial learning and memory in rats that showed deficits after ischaemic hippocampal damage induced by four vessel occlusion. Following ischaemia, rats were grafted with cells from a hippocampal (HPC OA 07) and a cortical (CTX OE 03) line. Six weeks later they were trained to find a submerged platform in a 2 m diameter circular pool, with 2 trials/day for a total of 6 days, followed by a probe trial with the platform removed, to test recall of its location. Sham grafted ischaemic rats took longer to find the platform, swam further in searching for it, and spent less time in the pool area where the platform was located, than non-ischaemic controls. The performance of grafted rats was intermediate between that of ischaemic and non-ischaemic controls, in general not differing significantly from either. However improvement above the level of ischaemic rats was very close to significance in key measures such as latency and path length, indicating a potential for reliable functional recovery.

Experimental Procedures

Surgery—four vessel occlusion: Rats were subjected to 4 VO by electrocauterising (Surgitron coagulator) the vertebral arteries under halothane anaesthesia (Merial Animal Health), and inserting ties around the carotids. The next day the carotids were lifted and clamped using serrefine aneurism clips for 20 minutes under brief halothane anaesthesia. Loss of righting reflex was maintained after the anaesthetic was discontinued, indicating 90%+reduction of cerebral blood flow. Controls were sham operated by cauterising the vertebral arteries and inserting ties, but without restriction of carotid blood flow. Body and head temperatures were monitored by rectal and head probes, recorded each minute and maintained at 37±2° C. by a homeothermic blanket (Harvard Apparatus) and overhead lamp.

Surgery—grafting: Rats were anaesthetised with ketamine (Ketalar, 80 mg/kg, Pharmacia and Upjohn Ltd. UK) and medetomidine (Domitor 0.5 mg/kg, Pfizer, UK) reversed after surgery by Atipamezole (Antisedan, 20 mg/kg, Pfizer, UK) and placed in a stereotaxic frame (Kopf, Tujunga CA). Homeothermic blankets (Harvard Apparatus) were used to maintain body heat. Holes were drilled in the skull to allow insertion of a 10-ul flat tipped Hamilton syringe. Two deposits of 2 ul at a density of 50,000 cells/ul were delivered at each site.

(i.e. 8 µl=400,000 cells/rat) over 2 minutes, at the following coordinates:

| AP: −3.3 | L: ±1.3 | V: −2.8 | 2"I/site |
|---|---|---|---|
| AP: −4.2 | L: ±3.4 | V: −3.1 | |

The syringe was slowly withdrawn after waiting for 2 minutes for dispersal. Fresh draws of suspension were taken for each site. Cells were freshly prepared and delivered twice a day (am, pm) to reduce deterioration on the bench.

All rats received immunosuppressive treatments consisting of cyclosporin A 10 mg/kg sc) in Cremophor EL (CSA/CEL) in a ratio of 1:4, starting the day before surgery and continuing for 3 days/week until perfusion. In addition rats were injected daily (20 mg sc) with prednisolone for 2 weeks, starting on the day of surgery.

Behavioural Testing for Spatial Memory Dysfunction:

Morris Water Maze, Animals were placed in a round pool (2 m) with a submerged platform (circle of 9 cm diam.) 2 cm under the surface of the water, with temperature held at 24±2° C. Animals were placed in one of four starting points and allowed to swim for a maximum of one minute. When animals climbed onto the platform they were allowed to remain for 10 seconds before being removed. Animals not finding the platform within one minute were placed on the platform. Animals were left on the platform for 20 seconds and then removed. The swim path was recorded by an image analysing system (HVS Image, UK). There were 2 trials per daily session separated by an interval of 8-10 minutes. Training was carried out over 9 days, in blocks of 4 and 3 days. However, on the $4^{th}$ day an apparatus failure resulted in unreliable data collection, so the results were discarded. The data analysed were therefore collected over 6 days counted as blocks 1-3 and 4-6, separated by a three-day interval. A probe trial was given 24 hous after the last acquisition trial, followed by a visible platform task on the next day. Three trials were given with the platform position marked by a cylindrical cue rising 10 cm above the surface of the water.

Histology

Perfusion and Sectioning:

Rats were transcardially perfused with 4% paraformaldehyde in 0.1 M sodium phosphate buffer (PBS, pH 7.4), brains were removed and stored in fixative at 4° C. overnight, then transferred to 30% sucrose in PBS. 50 µm serial sections were cut on a freezing microtome, collected in sucrose in 24 well culture plates and stored at −20° C. until processing.

Neuronal Loss:

Cell loss was quantified at the two levels of the graft/vehicle injection tracts, bilaterally, in NeuN labelled coronal sections across the medial-lateral extension of the CA1 field, including cell body and dendritic regions. Both the area of NeuN immunoreactivity and the intensity of staining were measured.

Grafted Cell Survival:

Grafted cells were identified by Human Nuclear (HuNuc) staining and counted in serial sections from the same regions of interest (ROI) used to estimate cell loss, in adjacent serial sections.

Results

The experiment used 33 rats, 10 with CTXOE03 grafts, 9 with HPCOA07 grafts, 8 with 4 VO and sham grafts and 6 sham-occluded and sham grafted controls.

Acquisition in the Water Maze

Five to six weeks after grafting, rats were trained to find a submerged platform in the water maze, with 2 trials/day separated by an interval of 8-10 minutes.

Latency: All groups showed a substantial linear decrease in time taken to find the platform over Blocks (F lin [1,29] =46.76. p<0.001) which levelled off as some groups reached asymptotic performance (F quad [1,29]=5.26, p<0.025). Steeper decrease in controls relative to lesioned rats resulted in an interaction between Groups and the linear trend of Blocks (F [3, 29]=4.07, p<0.02), and a trend towards an overall difference between Groups (F [3,29]=2.47, p=0.08). Comparison of means showed that intact controls differed from lesion controls (p<0.015), whilst grafted groups performed at control level. Although grafted groups showed a trend towards improvement relative to lesion-only rats (p=0.08, p=0.09), these differences were not significant. Grafted animals were therefore intermediate between intact and lesioned controls.

Histology Findings

Ischaemic lesions: The extent of CA1 cell loss was identified at two levels marked by injection tracts, and included dendritic and somatic fields. NeuN staining was mapped by area, and by intensity of immunofluorescence. Both measures indicated that ischaemic groups retained only 20-25% of cells seen in controls. Damage was uniform and localised to the CA1 field, and similar across all groups.

Grafted cell survival: HuNuc labelled grafted cells were seen in 2/10 rats with CTX OE 03 grafts and 6/9 rats in the HPC OA 07 group; 3 rats with HPC grafts also showed good migration. There was no evidence for differentiation of grafted cells into neurons.

Host brain changes: Sprouting, as measured by NF staining in the CA1 field, was significantly increased in the ischaemic control group, above the level of both sham operated and grafted animals. Grafts, therefore, reduced sprouting activity to control level. In contrast, host neurogenesis in the dentate gyrus was significantly increased in rats with HPC grafts, above levels seen in ischaemic controls. However, Ki67-IR was equivalent in lesioned controls and rats with CTX grafts, so there was no evidence for an effect of these cells on ongoing neurogenesis at the time of perfusion.

Correlations Between Histological and Behavioural Measures

Mean latency to find the platform over Blocks 1-3, 4-6, and over all 6 training blocks was correlated with extent of CA1 cell loss in terms of both area and intensity of NeuN-IR, in each of the four experimental groups. Within each group there was no relationship between the extent of CA1 cell loss, and increase in time taken to find the platform, by either measure of NeuN staining.

Similarly, the relationship between sprouting, as measured by area and intensity of neurofillament staining in the dentate gyrus, and latency to find the platform was examined. No significant association was found.

CONCLUSIONS

The three different neural stem cell lines described in this invention have been shown to be stable, and scalable, sources of cells for transplantation into patients with neurological disease. The range of potential therapies has been exemplified by showing functional recovery in a range of animal models of brain disease and degeneration. The typical success of these cell lines in restoring function in more than one disease model indicates that one or more of these cell lines may restore function in a variety of neurological diseases.

Great Britain Application Nos. 0421753.5, filed Sep. 30, 2004, 0425767.1, filed Nov. 23, 2004, and 0427830.5, filed Dec. 20, 2004, are each incorporated by reference herein in their entirety, including any figures, tables, nucleic acid sequences, amino acid sequences, and drawings.

All patents, patent applications, provisional applications, and publications referred to or cited herein are incorporated by reference in their entirety, including all figures and tables, to the extent they are not inconsistent with the explicit teachings of this specification.

We claim:

1. A cell line deposited under ECACC Accession No. 04110301.

* * * * *

UNITED STATES PATENT AND TRADEMARK OFFICE
CERTIFICATE OF CORRECTION

PATENT NO. : 7,419,827 B2
APPLICATION NO. : 11/283621
DATED : September 2, 2008
INVENTOR(S) : Sinden et al.

It is certified that error appears in the above-identified patent and that said Letters Patent is hereby corrected as shown below:

The Title Page should be deleted and substitute therefor the attached Title Page.

Signed and Sealed this

Twenty-sixth Day of May, 2009

JOHN DOLL
*Acting Director of the United States Patent and Trademark Office*

(12) United States Patent
Sinden et al.

(10) Patent No.: US 7,419,827 B2
(45) Date of Patent: Sep. 2, 2008

(54) CELL LINES

(75) Inventors: John Sinden, Surrey (GB); Kenneth Pollock, Surrey (GB); Paul Stroemer, Surrey (GB)

(73) Assignee: Reneuron Limited, Surrey (GB)

( * ) Notice: Subject to any disclaimer, the term of this patent is extended or adjusted under 35 U.S.C. 154(b) by 0 days.

(21) Appl. No.: 11/283,621

(22) Filed: Nov. 21, 2005

(65) Prior Publication Data

US 2006/0104959 A1 May 18, 2006

Related U.S. Application Data

(63) Continuation of application No. 11/238,702, filed on Sep. 29, 2005.

(30) Foreign Application Priority Data

| Sep. 30, 2004 | (GB) | ............................ 0421753.5 |
| Nov. 23, 2004 | (GB) | ............................ 0425767.1 |
| Dec. 20, 2004 | (GB) | ............................ 0427830.5 |

(51) Int. Cl.
*C12N 5/08* (2006.01)
*C12N 5/00* (2006.01)
*C12N 5/10* (2006.01)
*A61K 48/00* (2006.01)
*A01N 63/00* (2006.01)

(52) U.S. Cl. .................... 435/368; 435/325; 424/93.2; 424/93.7

(58) Field of Classification Search .................. None
See application file for complete search history.

(56) References Cited

U.S. PATENT DOCUMENTS

| 5,270,191 | A | 12/1993 | McKay et al. |
| 5,580,777 | A | 12/1996 | Bernard et al. |
| 5,690,927 | A | 11/1997 | Major et al. |
| 5,753,491 | A | 5/1998 | Major et al. |
| 5,770,414 | A | 6/1998 | Gage et al. |
| 5,817,773 | A | 10/1998 | Wilson et al. |
| 5,851,832 | A | 12/1998 | Weiss et al. |
| 5,958,767 | A | 9/1999 | Snyder et al. |
| 6,165,715 | A | 12/2000 | Collins et al. |
| 6,197,585 | B1 | 3/2001 | Stringer |
| 6,200,806 | B1 | 3/2001 | Thomson |
| 6,399,384 | B1 | 6/2002 | Jat |
| 6,465,215 | B1 | 10/2002 | Price et al. |
| 6,528,306 | B1 | 3/2003 | Snyder et al. |
| 6,569,421 | B2 | 5/2003 | Hodges |
| 2001/0001662 | A1 | 5/2001 | Sinden et al. |
| 2002/0028510 | A1 | 3/2002 | Sanberg et al. |
| 2002/0064873 | A1* | 5/2002 | Yang et al. ................ 435/325 |
| 2002/0123143 | A1 | 9/2002 | Toma et al. |
| 2002/0146821 | A1 | 10/2002 | Sanchez-Ramos et al. |
| 2003/0108535 | A1 | 6/2003 | Hodges |
| 2003/0143737 | A1 | 7/2003 | Morrison et al. |
| 2003/0147873 | A1 | 8/2003 | Sinden et al. |
| 2003/0203483 | A1 | 10/2003 | Seshi |
| 2004/0185429 | A1* | 9/2004 | Kelleher-Andersson et al. ................ 435/4 |
| 2005/0032213 | A1 | 2/2005 | Sinden et al. |

FOREIGN PATENT DOCUMENTS

| WO | WO 89/03872 A1 | 5/1989 |
| WO | WO 89/09816 A1 | 10/1989 |
| WO | WO 91/09936 A1 | 7/1991 |
| WO | WO 92/11355 A1 | 7/1992 |
| WO | WO 93/01275 A1 | 1/1993 |
| WO | WO 93/18137 A1 | 9/1993 |
| WO | WO 96/15226 A1 | 5/1996 |
| WO | WO 97/10329 A1 | 3/1997 |
| WO | WO 98/07841 A1 | 2/1998 |
| WO | WO 00/50568 A2 | 8/2000 |
| WO | WO 01/21790 A1 | 3/2001 |
| WO | WO 01/66698 A1 | 9/2001 |
| WO | WO 01/66781 A1 | 9/2001 |
| WO | WO 01/94541 A2 | 12/2001 |
| WO | WO 03/00868 A1 | 1/2003 |
| WO | WO 03/29432 A2 | 10/2003 |

OTHER PUBLICATIONS

Villa A, Navarro B, Martinez-Serrano A. Genetic perpetuation of in vitro expanded human neural stem cells: cellular properties and therapeutic potential. Brain Res Bull. Apr. 2002;57(6):789-94. Review.*

U.S. Appl. No. 11/178,216, filed Jul. 8, 2005, Sinden et al.

U.S. Appl. No. 09/913,443, filed Aug. 14, 2001, Price.

Allay, J.A. et al. "LacZ and interleukin-3 expression in vivo after retroviral transduction of marrow-derived human osteogenic mesenchymal progenitors" *Human Gene Therapy*, 1997, 8:1417-1427.

(Continued)

*Primary Examiner*—Michael Burkhart
(74) *Attorney, Agent, or Firm*—Saliwanchik, Lloyd & Saliwanchik

(57) ABSTRACT

The present invention relates to cells obtainable from cell lines having the ECACC Accession Nos 04091601, 04110301 and 04092302.

1 Claim, 3 Drawing Sheets